United States Patent
Haarer et al.

(10) Patent No.: US 7,081,364 B1
(45) Date of Patent: Jul. 25, 2006

(54) SUBSTRATE FOR PACKAGING PERISHABLE GOODS OR FOR APPLICATION ONTO SAME AND METHOD FOR DETERMINING THE QUALITY OF SAID GOODS

(76) Inventors: Dietrich Haarer, Hanweg 30, D-95448, Bayreuth (DE); Yoav Eichen, Avigavil Street 20, 32000, Haifa (IL)

( * ) Notice: Subject to any disclaimer, the term of this patent is extended or adjusted under 35 U.S.C. 154(b) by 0 days.

(21) Appl. No.: 09/601,374

(22) PCT Filed: Jan. 27, 1999

(86) PCT No.: PCT/EP99/00517

§ 371 (c)(1), (2), (4) Date: Sep. 11, 2000

(87) PCT Pub. No.: WO99/39197

PCT Pub. Date: Aug. 5, 1991

(30) Foreign Application Priority Data

Jan. 28, 1998 (DE) ................................. 198 03 208

(51) Int. Cl.
G01N 21/78 (2006.01)
(52) U.S. Cl. .................. 436/164; 436/166; 436/4; 422/50; 422/55; 422/56; 422/57
(58) Field of Classification Search ............. 436/2, 436/164, 166, 169, 4; 422/50, 55, 56, 57, 422/82.05
See application file for complete search history.

(56) References Cited

U.S. PATENT DOCUMENTS

| | | | |
|---|---|---|---|
| 3,999,946 A | 12/1976 | Patel et al. | 23/253 TP |
| 4,389,217 A | 6/1983 | Baughman et al. | 436/2 |
| 4,805,188 A * | 2/1989 | Parker | 374/141 |
| 5,053,339 A | 10/1991 | Patel | 436/2 |
| 5,057,434 A | 10/1991 | Prusik et al. | 436/2 |

FOREIGN PATENT DOCUMENTS

| | | |
|---|---|---|
| DE | 198 03 208 A1 | 8/1999 |
| EP | 0 117 390 | 9/1984 |
| EP | 0 177 432 | 4/1986 |
| JP | 63035684 A | 2/1988 |
| JP | 1204902 A | 8/1989 |
| JP | 07165881 A | 6/1995 |
| JP | 9-229782 | 9/1997 |
| WO | WO 92/09870 | 6/1992 |
| WO | WO 96/06643 | 3/1996 |

OTHER PUBLICATIONS

Journal of Physical Chemistry, "Photochromism and Thermochromism Driven by Intramolecular Proton Transfer in Dinitrobenzylpyridine Compounds" Corval et al. 1996.*
Journal of Physical Chemistry, "Quantum Chemical Investigation of the Thermal and Photoinduced Proton-Transfer Reactions of 2-(2,4-Dinitrobenzy)pyridine" Frank et al. 1996.*
Michael, Scherl et al., Proton Transfer Processes in Well-Defined Media: Experimental Investigation of Photoinduced and Thermal Proton-Transfer Processes in Single Crystals of 2-(2,4-Dinitrobenzyl) pyridine Derivatives, J. Phys. Chem. 1996, pp. 16175-16186.

* cited by examiner

*Primary Examiner*—Jill Warden
*Assistant Examiner*—LaToya Cross
(74) *Attorney, Agent, or Firm*—Young & Basile, P.C.

(57) ABSTRACT

The invention relates to a substrate for packaging of or for attachment to products which are sensitive to aging and temperature, having a planar time-temperature integrator comprising a matrix and at least one reversible indicator embedded therein, which has photochromic properties on the basis of transfix reactions, arranged in the region of the substrate.

24 Claims, 7 Drawing Sheets

Crystal (T=298K)

$t_1$=5200 s Crystal (T=298K) $t_1$=36000 s
$t_2$=24200 s $t_2$=1700000 s

Crystal (T=298K)

t=16000s Crystal(T=298K) t=73000 s

Crystal (T=298K)

t=23200s Crystal(T=298K) t=427 s

Crystal (T=298K) t=427 s

318 K →

Phase A          Phase B

SUBSTRATE FOR PACKAGING PERISHABLE GOODS OR FOR APPLICATION ONTO SAME AND METHOD FOR DETERMINING THE QUALITY OF SAID GOODS

The invention relates to a substrate for packaging of or attachment to perishable products which are sensitive to aging or temperature, such as foodstuffs or medicaments, and a process for determination of quality thereof.

When using transitory materials, it is often desirable to determine the age and the current shelf status of the materials. If attachment of an expiry date to the packaging has been considered adequately beforehand, this procedure today is too imprecise and has too little security against falsification for a number of products. In particular the status of transitory products is usually not only a function of time, but also of further parameters, such as in particular the temperature.

U.S Pat. No. 3,999,936 takes up this problem and proposes attaching an indicator showing the time-temperature previous history to the perishable products. The originally colourless indicator based on acetylene shows a characteristic, irreversible discolouration, depending on period of storage and storage temperature of the product, by means of which conclusions can be made on the quality of the stored perishable product.

However, its tedious handling stands in the way of further expansion of the process known from U.S. Pat. No. 3,999,946. Hence, the indicator must be stored at very low temperatures and in the dark until it is attached to the product to initially delay the onset of the actual required time-temperature effect initiated by indicator synthesis. The indicator reaction itself proceeds auto-catalytically and strongly non-linearly, which makes precise evaluation more difficult. The disadvantage is also that the indicator reaction is irreversible, so that use is excluded for multiple-use packages funding increasing expansion.

Starting from this and further disadvantages of the state of the art, the object of the invention is to indicate a substrate for packaging; of or attachment to perishable products, which permits determination of quality of the products, is simple to handle and furthermore can also be used several times. The object is also to provide a process for determination of quality which permits safe and precise determination for the shelf status of the perishable product.

This object is achieved by a substrate for packaging of or for attachment to products which are sensitive to aging and temperature, having a time-temperature integrator arranged in the region of the substrate, wherein the time-temperature integrator contains a matrix and at least one reversible, crystalline indicator embedded therein, which has photochromic properties on the basis of transfer reactions in crystalline materials, and wherein further the reversible indicator is characterized by discoloration following photo-induced coloration thereof, the discoloration proceeding as a function of both time and temperature. This object is further achieved by a process for determining the quality of products which are sensitive to aging and temperature and are provided with a substrate according the present invention, the process comprising the steps of effecting photo-induced coloration of the reversible indicator, and determining the degree of time-related or temperature-related discoloration and the quality of the product taking into account the degree of discolouration. The sub-claims relate to preferred embodiments and further developments of the invention.

A substrate for packaging of or for attachment to products which are sensitive to aging and temperature, having a planar time-temperature integrator arranged in or on or below the substrate, allows a reliable determination of quality of perishable products if the time-temperature integrator contains at least one reversible indicator, which is embedded in a matrix and has photochromic properties on the basis of transfer reactions. Transfer reaction is generally understood to mean those reactions which take place during the change in the atomic characteristic activities, which involves the relocation of at least one atom. An example is the transfer of a hydrogen atom (or a proton or hydride). Here the above-mentioned species of a "donor" group is transferred to an "acceptor" group and thus forms a tautomeric compound. During transfer of other groups, isomeric or charged species may be formed during the transfer reaction.

On the basis of the photochromic properties, the indicator can be coloured in photo-induced manner by irradiating with photons of a certain energy range, wherein a time-dependent and temperature-dependent discolouration occurs following colouration. The required reversibility of the indicator reaction allows renewed photo-induced colouration after or during discolouration. Colouration of the indicator may be effected at a defined point in time, preferably for example immediately before or after production or packaging of the perishable material.

In contrast to the indicator materials of the state of the an, the time-temperature clock can thus be started defined at a required point in time and does not begin to proceed irreversibly even at the point in time of indicator synthesis. In addition, according to the invention the colouration process is not considered, but the reverse reaction, that is discolouration.

The time-temperature integrator may be provided with a filter to avoid undesirable renewed coloration of the indicator after starting the time-temperature clock by filtering out certain wavelength ranges. In addition, a further, irreversible indicator may be arranged, for example next to or above the reversible indicator, to secure against falsification. The further indicator indicates with reversible colouration that the reversible indicator has been coloured again after production or packaging of the perishable goods.

The reversible indicator may be produced both as a solid, for example in the form of glasses or crystals, and in solution Production its possible both as pure substance and at the same time with the matrix. Above all, crystalline indicators show adequately long discolouration times of typically one day and longer for conventional commercial applications. Amorphous indicators usually show discolouration times of less than one day. By selecting the synthesis conditions or varying the crystal growth processes, the discolouration times can be set specifically between almost instantaneous discolouration up to days, weeks or months.

Indicators having more than one characteristic time domain may also be produced. Such indicators may have, for example a phase transition, wherein the different phases show different discolouration behaviour. The simultaneous use of two or more indicators having different time domains is likewise possible.

The indicators are preferably embedded in a carrier matrix. The matrix term has a very broad meaning according to the invention, and includes, for example also the substrate. Hence, it is conceivable to incorporate the indicators directly in a region of the substrate.

The actual determination of quality of products which are sensitive to aging or temperature initially assumes photoinduced colouration of the reversible indicator. Colouration may take place before application of a filter or the irreversible indicator or from a side of the substrate opposite the filter. At a later point in time, the degree of time-related or temperature-related discolouration is then measured and the product quality is concluded therefrom. During evaluation with the aid of the human eye, it may be advantageous if a reference scale is arranged, for example next to or below the substrate, which assigns a certain quality grade, a certain point in time etc., to a certain degree of discolouration.

Further details and preferred embodiments of the invention can be seen from the figures and exemplary embodiments.

The substrates of the invention are suitable for packaging of or attachment to perishable products, such as foodstuffs (for example frozen goods), medicaments, drugs, transplant organs and transitory materials. The time-temperature indicator connected to the substrate may be designed to be planar or, far example in the form of a pattern or logo. Although all components can be recycled, disposal is in principle harmless, since no poisonous or pollutant materials have to be used.

The photochromic indicator reactions may be based, for example on reversible electron transfer or on the reversible transfer of a charged or uncharged hydrogen atom (proton, hydride) or a hydrogen isotope (deuterium, tritium). Transfer is preferably of protons, deuterons, halogen radical ions or simple chemical groups, such as methyl groups.

Figure 1:
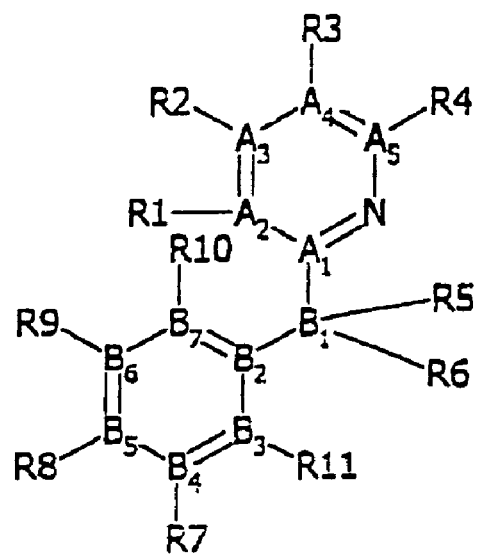
FIG. 1 shows a skeletal structure of a photo-induced reversible indicator.

FIG. 1 shows the skeletal structure of a reversible indicator.

The radicals are $A_1$–$A_5$ preferably a carbon atom or heteroatom, such as for example N, S, O etc.; $R_1$–$R_4$ is an atom, such as hydrogen or its isotopes or also Cl, F, Br atoms; or other substituents, such as for example alkyl groups, in particular methyl groups or aryl groups, in particular phenyl groups. $R_5$ is H, D or Y or substituents, such as for example Cl, F, Br etc. or an alkyl group, in particular methyl group or an aryl group, in particular phenyl or pyridine. $R_6$ is H, D, Y and $B_1$–$B_7$ is a carbon atom or heteroatom, such as for example N, S, O etc., $R_1$–$R_{10}$ are preferably atoms, such as for example hydrogen atoms or their isotopes or one or more Cl, F, Br, amino groups or nitro groups etc. or one or more substituents, such as for example alkyl groups, in particular methyl or aryl groups, in particular phenyl. $R_{11}$ is a nitro group or a cyano group or a carboxylic acid group or a variant, such as for example an ester, amide, ketone or aldehyde group.

$A_1$–$A_5$ is particularly preferably a carbon atom and $R_1$–$R_4$ hydrogen (pyridine). The pyridine ring may also be part of an extended molecular system (quinoline, phenanthroline etc.). in addition, the variants preferably designated further As are replaced by N, such as for example pyrazine, pyridazine, pyrimidine, tetrazine, pentazine etc.

The radical $R_{11}$ is at least one $NO_2$, $NH_2$ or CN group. It is preferable if an $NO_2$ group is present which forms an ortho-vitro phenyl group. Furthermore, the phenyl group may be part of a larger, extended molecular system. In addition, one or more carbon atoms of the phenyl ring may be replaced by heteroatoms.

Figure 2:
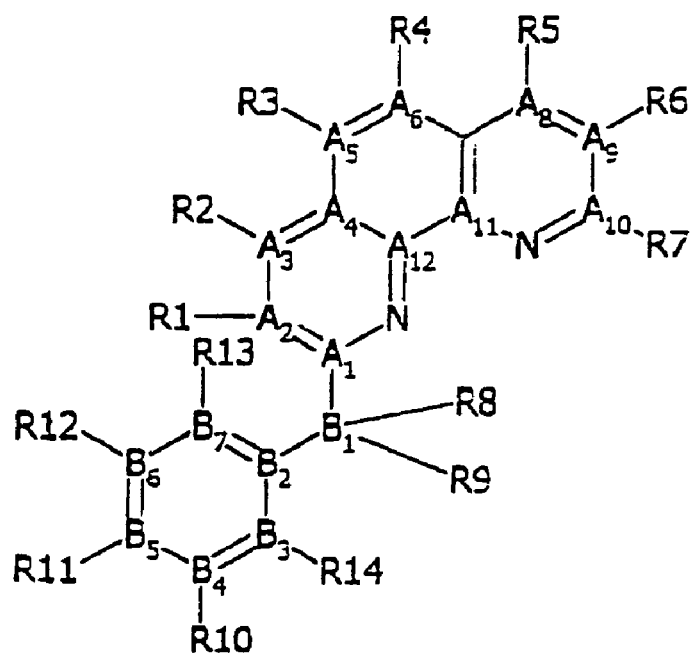
FIG. 2 shows a further skeletal structure of a photo-induced reversible indicator.

A further suitable skeletal structure is shown in FIG. 2. The phenanthroline group is essential here.

$A_1$–$A_{12}$ thus denotes a carbon atom or heteroatom, such as for example N, S, O etc., $R_1$–$R_7$ an atom, such as hydrogen or its isotopes or Cl, F, B or other substituents, such as for example alkyl groups, in particular methyl or aryl groups, in particular phenyl. $R_8$ is H, D, T or a substituent, such as for example Cl, F, Br etc. or an alkyl group, in particular methyl or an aryl group, in particular phenyl or pyridine. $R_9$=a nitro group or a cyano group or a carboxylic acid group or a variant, such as for example an ester, amide, ketone or aldehyde group. $R_{10}$–$R_{13}$ is an atom, such as for example hydrogen or its isotopes or one or more CL, F, Br, amino groups or nitro groups etc. or one or more substituents, such as for example alkyl groups, in particular methyl or aryl groups, in particular phenyl.

The phenanthroline group bonded to $B_1$ is essential.

The phenanthroline group may have different substituents $R_1$–$R_7$ which are hydrogen in the simplest case, but which may also consist of methyl groups, phenyl groups. In addition, the phenanthroline group may be part of an extended molecular system (such as for example for quinoquinolines). Furthermore, one or more As of the phenanthroline molecule may be replaced by heteroatoms (for example nitrogen for azaphenanthroline etc.) Compounds having other heteroatoms are also suitable here.

It generally applies that different length discolouration times may be achieved depending on the type of photochemically induced transfer reaction and in particular depending an binding strength of the "acceptor" of the transferred species.

Figure 3:
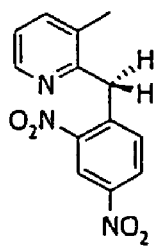
FIG. 3 shows examples of reversible indicators.
Figure 3:
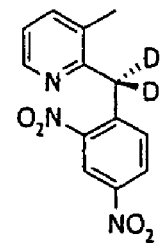
Figure 3:
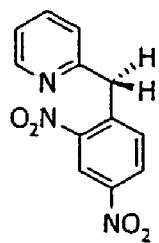
Figure 3:
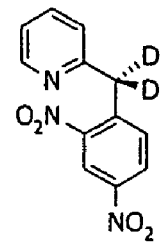
Figure 3:
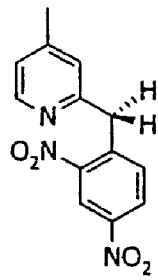
Figure 3:
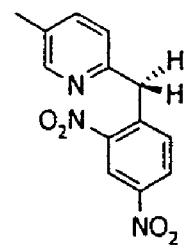
Figure 3:
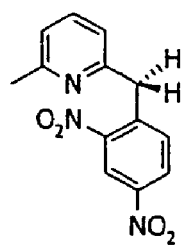

FIG. 3 shows examples of indicators having the skeletal structure according to FIG. 1, in each case having the associated typical discolouration times at a temperature of 298° K. Provided, where two times are indicated, they are systems which have two different phases.

Depending on application, a compound having optimised time-temperature behaviour may be used.

Figure 4:
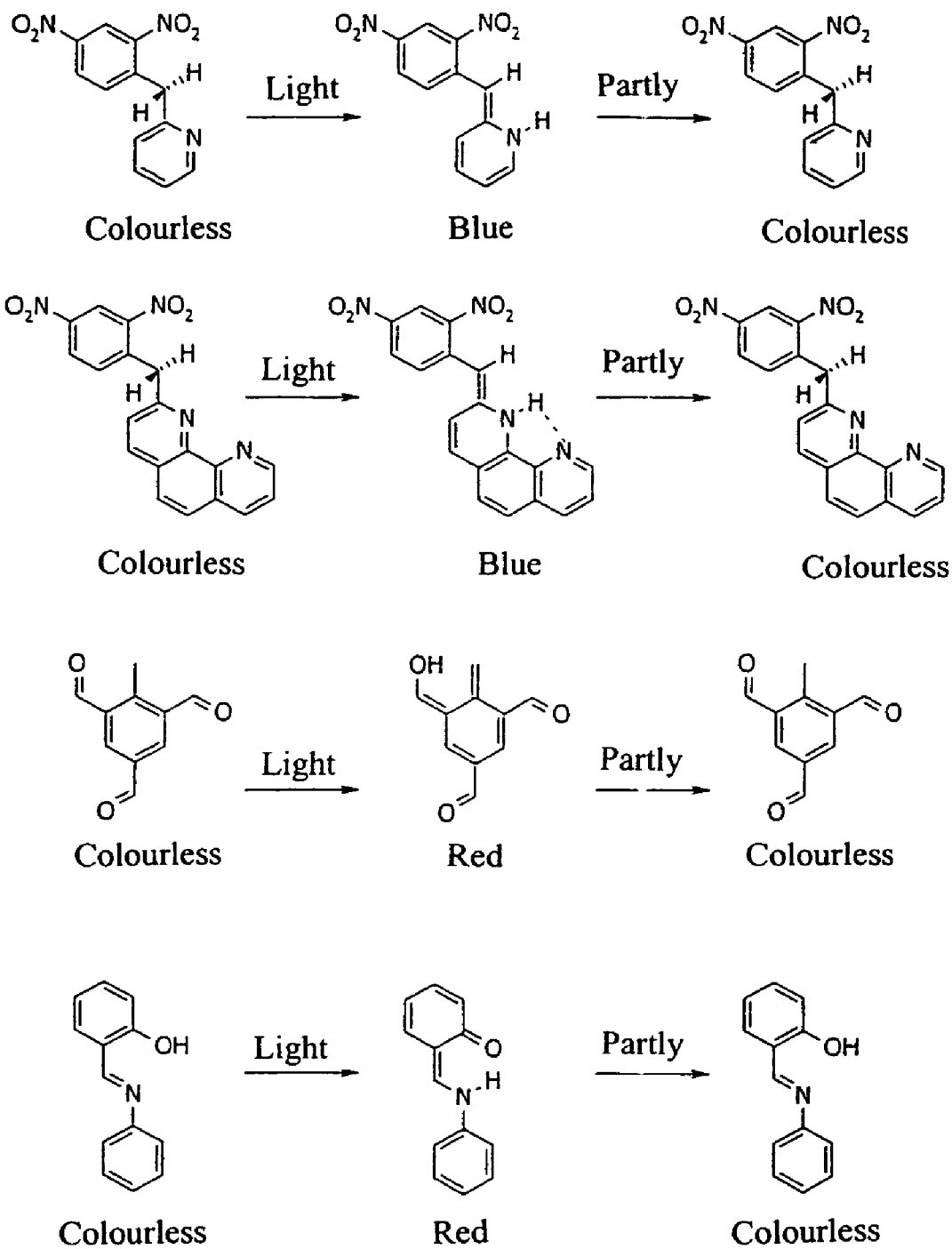
FIG. 4 shows examples of proton transfer reactions.
Figure 5:
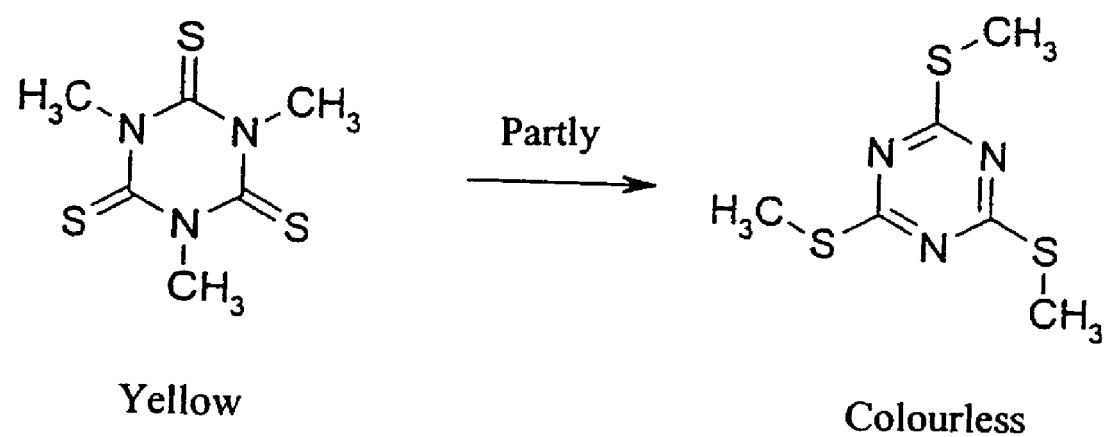
FIG. 5 shows an example of a methyl group transfer reaction.
Figure 6:
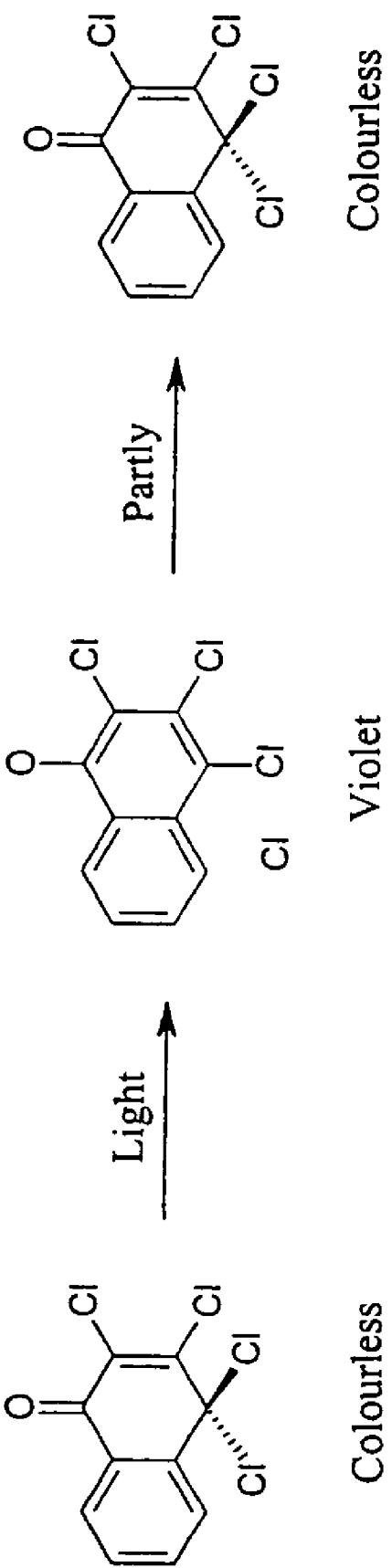
FIG. 6 shows an example of a halogen transfer reaction.

Examples of proton transfer reactions are sketched in FIG. 4. The initially colourless indicator is thus irradiated with UV light or near UV light, whereupon a proton transfer and a thus concomitant indicator colouration takes place. This photo induced proton transfer then proceeds back in the other direction as a function of time and temperature, so that the indicator is discoloured successively. Analogous reactions, based on the transfer of methyl groups or halogen radicals, are shown in FIGS. 5 and 6.

Figure 7:
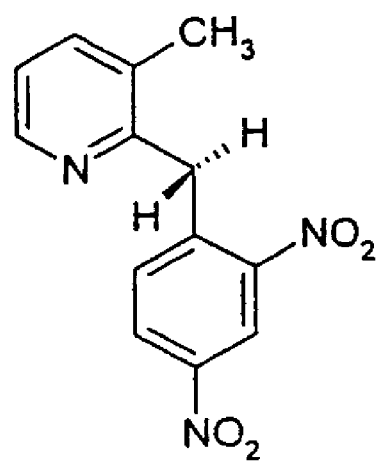
FIG. 7 shows an indicator system having two characteristic time domains.
Figure 7:
Figure 7:

FIG. 7 shows a system which has two crystalline phases and two different characteristic time domains. Phase transition from a first crystalline phase with long discolouration times to a second crystalline phase having a discolouration time which is shorter by a factor 10 is effected at a temperature of 318° K. Other phase transitions, for example crystal fusion, show similar properties.

Figure 8:
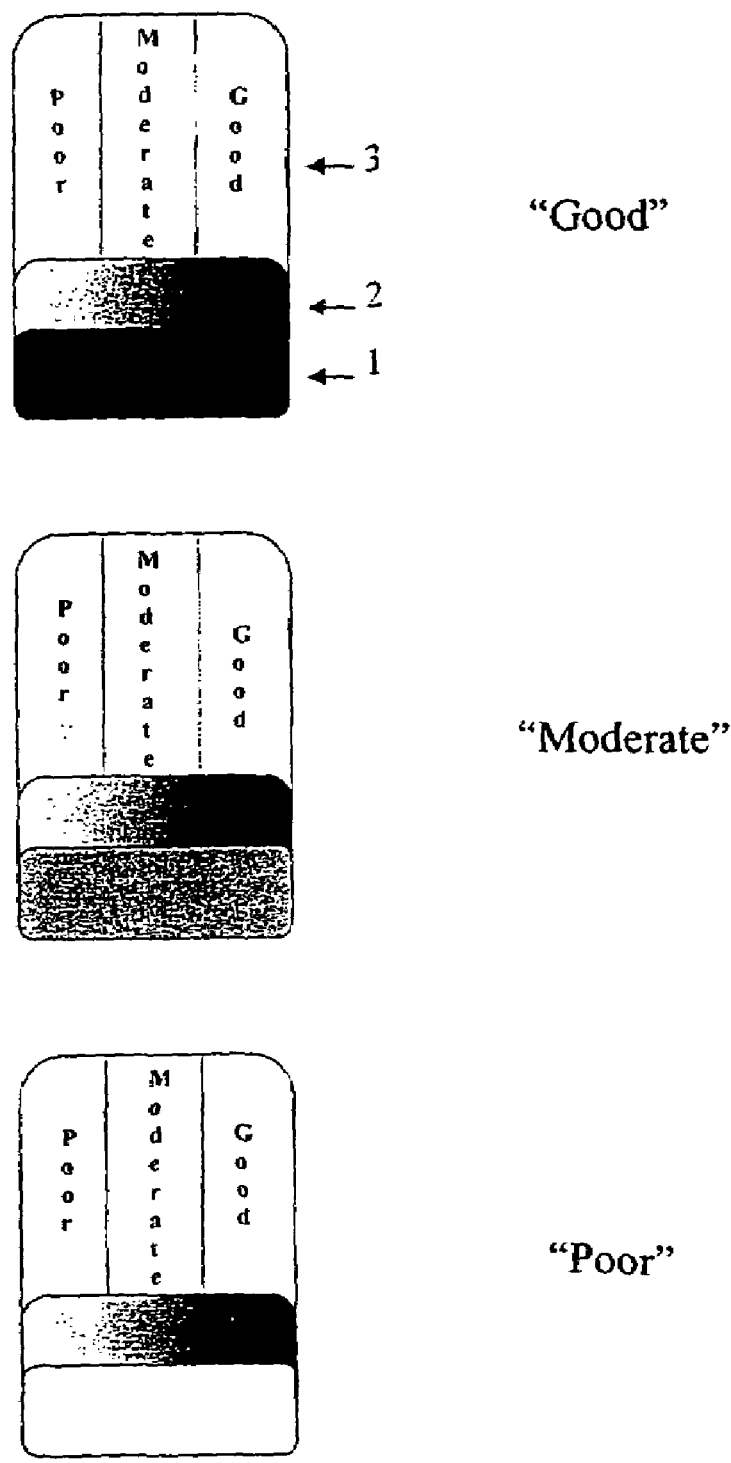
FIG. 8 shows a time-temperature integrator with reference scale in plan view.

FIG. 8 shows the procedure for determination of quality with the aid of a time-temperature integrator 1. A primed reference scale 2, which permits an absolute determination of quality grades by means of the likewise primed assignment scale 3, is arranged above the time-temperature integrator 1. The time-temperature integrator is advantageously arranged on a light substrate to facilitate reading.

Both inorganic and organic materials, preferably those which are known from conventional layer and packaging techniques, are suitable as substrate materials. Polymers, glass, metals, paper, cardboard etc. may be mentioned by way of example. The substrate may form at the same time the packaging material for the perishable products or be attached to the packaging material or directly to the product.

The reversible indicator is introduced either directly into the substrate material, wherein the substrate assumes the matrix function and is preferably arranged on or below the substrate in the form of an indicator-doped matrix The reversible indicator may be embedded in the matrix in the form of small crystallites or in solid solution. The matrix is, for example a polymer (PVC, PMMA, PEO, etc.) or glass-like film. Indicator-doped matrices can also be produced by means of sod-gel techniques.

The irreversible photosensitive indicator intended as falsification security may be applied to the time-temperature integrator as a coating. For example pyrrole derivatives, such as 2-phenyl-di(2-pyrrole)methane, are suitable irreversible indicators. This material becomes irreversibly red if it is exposed to UV light.

After applying the irreversible indicator, a colour filter is arranged on the time-temperature integrator. Yellow filters, which are permeable only to light having typical wavelengths of over 430 nm. are suitable for UV-sensitive indicators, The photo-induced charging of the time-temperature integrator is preferably effected before applying the irreversible indicator and the filter. Alternatively, the intention may also be to charge the time-temperature integrator from a substrate side not covered by a filter.

Some production examples for time-temperature integrators are illustrated in detail below:

Polymer films doped with 2-(2,4-dinitrobenzyl)pyridine:
100 mg of 2-(2,4-dinitrobenzyl)pyridine, α-DNBP, are dissolved in 50 ml of tetrahydrofuran (solution A). 330 mg of PVC (for example molecular weight 100,000) are dissolved in 50 ml of tetrahydrofuran and filtered (solution B). Solution A and solution B are mixed in a suitable container, the substance is cast into a thin film and the latter is dried in the dark at about 40° C. The film being formed is about 100 μm thick, transparent and it shows excellent mechanical and optical properties. The films may be produced in different shapes and thicknesses. The transparent doped film becomes coloured during activation (for example UV radiation) and is discoloured at a rate which is characteristic for the particular material selected, depending on the time and temperature. The system is reversible over many cycles.

Pure organic glasses of 2-(2,4-dinitrobenzyl)pyridine compounds:
3 mg of a glass-forming material, such as for example derivatives of 2-(2,4-dinitrobenzyl)pyridine (for example as heteroaryl-substituted material in 6 position) are melted between 2 transparent glasses or between two flexible films, and after melting, quenched, for example by cooling in liquid nitrogen. The glass being formed is fully transparent and has variable thickness. The glass is stable for long periods and at very different temperatures.

Polymer "pellets" doped with 2-(2,4-dinitrobenzyl)pyridine:
2 mg of 2-(2,4-dinitrobenzyl)pyridine, α-DNBP, are ground to a very fine powder. In order to determine the gradation of grinding, thin following tests may be undertaken:
1. Irradiation of the crystals (350 nm<λ<400 nm)
2. Grinding of the crystals
3. Irradiation of the crystals (350 nm<λ<400 nm)
4. Grinding of the crystals
5. If the colour of the powder remains the same, the grinding process is interrupted.

The size of the crystals is then just a few μm. The ground dust is mixed with 100 mg of a suitable matrix, such as for example PS, PED etc. and placed in a press. The chamber with the material is then evacuated and exposed to a pressure of 15–20 kbar (for about 30 minutes). The result is a 1–2 mm thick tablet which appears white. The thin tablet becomes deep blue on irradiation by appropriate light (preferably UV). The tablet is then discoloured again as a consequence of time and temperature. The system is reversible and may, if required, be cycled many times.

All above-mentioned samples are not sensitive to light if they are coated with an inexpensive, yellow polymer or cellophane film. An indicator, which may also be used in daylight, may be produced in this manner.

What is claimed is:

1. Substrate for packaging of or for attachment to products which are sensitive to aging and temperature, having a time-temperature integrator arranged in the region of the substrate, wherein the time-temperature integrator contains a matrix and at least one reversible, crystalline indicator embedded therein, which has photochromic properties on the basis of transfer reactions in crystalline materials, and wherein further the reversible indicator is characterized by discoloration following photo-induced coloration thereof, the discoloration of the reversible indicator proceeding as a function of both time and temperature.

2. Substrate according to claim 1, wherein the substrate is a packaging material.

3. Substrate according to claim 1, wherein the transfer reactions are based on the transfer of charged or uncharged hydrogen atoms or hydrogen isotopes.

4. Substrate according to claim 1, wherein the reversible indicator has a skeletal structure according to the general formula I;

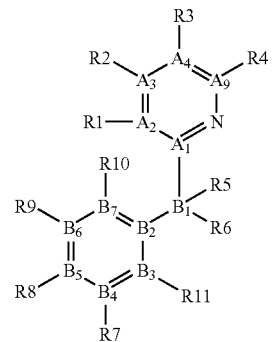

wherein $A_1$–$A_5$=carbon atom and/or heteroatom $R_1$–$R_4$=hydrogen atom and/or isotope thereof, and/or Cl, F, Br, or a substituent selected from the group consisting of alkyl groups, methyl or aryl groups, and phenyl groups $R_5$=hydrogen atom or isotope thereof, or a substituent selected from the group consisting of Cl, F, Br, an alkyl group, a methyl group, an aryl group, phenyl group, and pyridine $R_6$=hydrogen atom or isotope thereof $B_1$–$B_7$=carbon atom and/or heteroatom $R_1-R_{10}$=hydrogen atom and/or an isotope thereof, and/or one or more Cl, F, Br, amino groups, nitro groups, or one or more substituents selected from the group consisting of alkyl groups, methyl or aryl groups, and phenyl groups, $R_{11}$=nitro group or a cyano group or a carboxylic acid group or a variant selected from the group consisting of an ester, amide, ketone or aldehyde group.

5. Substrate according to claim 1, wherein the reversible indicator has a skeletal structure according to the general formula II:

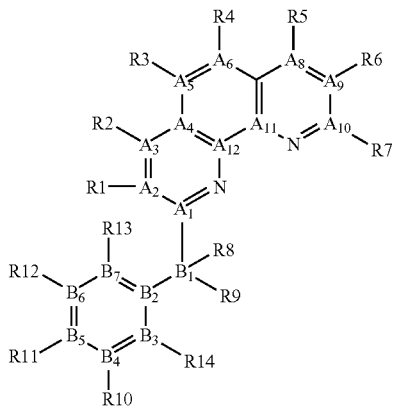

wherein $A_1-A_{12}$=carbon atom and/or a heteroatom $R_1-R_7$=hydrogen atom and/or isotope thereof, and/or Cl, F, B, or substituents selected form the group consisting of alkyl groups, methyl or aryl groups, and phenyl groups $R_8$=hydrogen atom or isotope thereof, or a substituent selected from the group consisting of Cl, F, Br, an alkyl group, phenyl group, and pyridine $R_9$=hydrogen atom or isotope thereof $B_1-B_7$=carbon atom and/or heteroatom $R_{10}-R_{13}$=hydrogen atom and/or isotope thereof, and/or one or more Cl, F, Br, amino groups, nitro groups, or one or more substituents selected from the group consisting of alkyl groups, methyl or aryl groups, and phenyl groups $R_{14}$=a nitro group, a cyano group, a carboxylic acid group, an ester, an amide, a ketone, or an aldehyde group.

6. Substrate according to claim 5, wherein in the general formula II, $R_4$=NO$_2$ and 2-4 NO$_2$ groups are present.

7. Substrate according to claim 4, wherein in the general formula I, $R_4$=NO$_2$ and 2-4 NO$_2$ groups are present.

8. Substrate according to claim 1, wherein the transfer reactions are based on large, charged or uncharged groups.

9. Substrate according to claim 1, wherein the transfer reactions are based on a charged or uncharged halogen atom.

10. Substrate according to claim 1, wherein the reversible indicator has more than one characteristic time domain.

11. Substrate according to claim 1, wherein at least two reversible indicators having different characteristic time domains are embedded in the matrix.

12. Substrate according to claim 1, wherein at least one irreversible indicator having photochromic properties is arranged in the region of the reversible indicator.

13. Substrate according to claim 1, wherein the time-temperature integrator has a filter which is impermeable to light which effects photo-induced coloration of the reversible indicator.

14. Substrate according to claim 13, wherein the filter is impermeable to light in the wavelength range of below approximately 430 nm.

15. Substrate according to claim 1, wherein the substrate includes a reference scale arranged in the region of the time-temperature integrator.

16. Substrate according to claim 1, wherein the matrix is a polymer film.

17. Substrate according to claim 1, wherein the substrate is a polymer film.

18. Substrate according to claim 1, wherein a substrate region forms the matrix for the reversible indicator.

19. Process for determination of quality of products which are sensitive to aging and temperature comprising the steps of:
  a) providing a substrate for packaging of or for attachment to a product which is sensitive to aging and temperature, having a time-temperature integrator arranged in the region of the substrate, wherein the time-temperature integrator contains a matrix and at least one reversible, crystalline indicator embedded therein, which has photochromic properties on the basis of transfer reactions in crystalline materials, and wherein further the reversible indicator is characterized by discoloration following photo-induced coloration thereof, the discoloration of the reversible indicator proceeding as a function of both time and temperature;
  b) effecting photo-induced coloration of the, reversible indicator; and
  c) determining the degree of time-related and temperature-related discoloration and the quality of the product taking into account the degree of discoloration.

20. Process according to claim 19, wherein the determination of the quality of the product is effected by evaluating the degree of discoloration with the aid of a reference scale.

21. Process according to claim 19, further comprising the step of providing an irreversible indicator having photochromic properties, the irreversible indicator arranged in the region of the reversible indicator, and wherein further the irreversible indicator is applied after photo-induced coloration of the reversible indicator.

22. Process according; to claim 19, further comprising the step of providing the time-temperature integrator with a filter that is impermeable to light which effects photo-induced coloration of the reversible indicator, and wherein further the filter is applied after photo-induced coloration.

23. Process according to claim 19, wherein the photo-induced coloration of the reversible indicator is effected by UV or near UV light.

24. Process according; to claim 19, wherein the photo activation of the time-temperature integrator is effected by irradiation of the side of the time-temperature integrator opposite the filter.

* * * * *